United States Patent [19]

Ratts

[11] 3,961,934
[45] June 8, 1976

[54] METHOD FOR INCREASING THE SUCROSE CONTENT OF GROWING PLANTS

[75] Inventor: Kenneth Wayne Ratts, Creve Coeur, Mo.

[73] Assignee: Monsanto Company, St. Louis, Mo.

[22] Filed: Dec. 19, 1974

[21] Appl. No.: 534,268

[52] U.S. Cl. ............................................. 71/86
[51] Int. Cl.$^2$ ......................................... A01N 9/36
[58] Field of Search ................................ 71/86, 76

[56] References Cited
UNITED STATES PATENTS

| | | | |
|---|---|---|---|
| 3,556,762 | 1/1971 | Hamm | 71/86 |
| 3,826,641 | 7/1974 | Porter | 71/86 |
| 3,853,530 | 12/1974 | Fronz | 71/76 |
| 3,894,861 | 7/1975 | Hartman | 71/86 |

OTHER PUBLICATIONS

Ivanov et al., "Reaction Between N-methylol etc.," (1968), CA69, No. 87090a, (1968).
Arbuzov, et al., "Reaction of the N-(hydroxymethyl) etc.," (1967), CA68, No. 49686w, (1968).
Pralon, et al., "Prep. of a Phosphonic Analog, etc.," (1970), CA74, No. 31944t, (1971).

*Primary Examiner*—Glennon H. Hollrah
*Attorney, Agent, or Firm*—Arnold H. Cole; Donald W. Peterson

[57] ABSTRACT

The sucrose content of sugar cane plants is increased by treating the plants, prior to harvest, with N-acetyl or chloroacetyl derivatives of aminomethylenephosphonic acid, and certain esters and salts thereof.

19 Claims, No Drawings

METHOD FOR INCREASING THE SUCROSE CONTENT OF GROWING PLANTS

This invention relates to a method for increasing the sucrose content of growing plants. More particularly, this invention is concerned with a method wherein sugar cane plants are subjected to a chemical treatment which serves to increase the amount of harvestable sucrose in said plants.

It is known that certain phosphonic acid derivatives have been used to enhance the yield of sucrose from sugar cane plants. For example, U.S. Pat. Nos. 3,619,166 and 3,712,936 describe the use of various carbamoylphosphonates for this purpose. U.S. Pat. No. 3,556,762 teaches the same use for amino acid derivatives of aminoalkylenephosphonic acids, such compounds requiring the presence of three acid groups on the central nitrogen atom. Similarly, the use of derivatives of N-phosphonomethylglycine for treatment of sugar cane is disclosed in U.S. Pat. No. 3,853,530, these compounds requiring the presence of two acid groups on the central nitrogen atom.

It has now been found that N-acetyl or chloroacetyl derivatives of aminomethylenephosphonic acid, and certain salts and esters thereof, when applied to sugar producing plants in the manner hereinafter described, serve to increase the amount of recoverable sucrose in such plants. It is believed that this desirable effect results from an action of the chemical to reduce or retard further vegetative growth of the treated plant just prior to its harvest. Thus, the reducing sugars which are stored in the plant are not used as energy for plant growth but are rather converted to recoverable sucrose.

The chemical substances employed in practicing the method of this invention consist of compounds illustrated by the formula

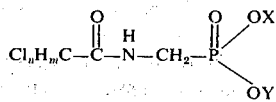

wherein X and Y represent hydrogen or lower alkyl, $n$ is an integer from zero to three, $m$ is an integer from zero to three, and the sum of $m + n$ is three; and certain salts of the compounds, which salts are selected from the group consisting of alkali metal, ammonium, lower alkyl and lower alkanol amine, aniline and substituted aniline. As employed herein, the term "lower" designates those aliphatic radicals which have up to four carbon atoms in a straight or branched chain.

The salts which are encompassed by this invention can be either the mono or di salts of the cations recited above. As specifically regards the amine salts, it should be understood that these include the primary, secondary and tertiary amines of the defined alkyl and alkanol groups.

The N-acetyl or chloroacetyl aminomethylenephosphonic acids of this invention can be readily prepared by first reacting an appropriately chlorinated methylol acetamide with phosphorus trichloride. The resultant intermediate is then converted to the desired product by treatment with water after standing in a closed vessel for a long period of time. Proportions of reactants, reaction conditions and the like are described in detail in U.S. Pat. Nos. 2,304,156 and 2,328,358.

The acids prepared by the method just described can be esterified in accordance with well known procedures. Similarly, said acids can be readily converted to their salts by addition of the appropriate amine or alkali metal hydroxide.

The N-acetyl or chloroacetyl aminomethylenephosphonic acids of this invention can also be prepared by reacting acetyl chloride or acetic anhydride (with chlorination on the acyl group as desired) with aminomethylenephosphonic acid. Correspondingly, if the starting material is a phosphonate ester, the reaction product will be an ester of this invention. Further, where said ester product contains the trichloroacetyl group on the nitrogen, it can be hydrolyzed to the acid under acidic conditions.

Following the above synthesis routes, or using other alternative procedures which may be available, illustrative compounds of the present invention which can be prepared include:

1. N-trichloroacetyl aminomethylenephosphonic acid, m.p. 196°–198°C.
2. N-dichloroacetyl aminomethylenephosphonic acid, m.p. 133°–135°C.
3. Diethyl N-dichloroacetyl aminomethylenephosphonate
4. Diethyl N-chloroacetyl aminomethylenephosphonate, m.p. 67°–69°C.
5. Monopotassium salt of N-trichloroacetyl aminomethylenephosphonic acid, m.p. ~ 140°C. (dec.)
6. Monoisopropylamine salt of N-trichloroacetyl aminomethylenephosphonic acid, m.p. ~ 180°C. (dec.)
7. Monoethanolamine salt of N-trichloroacetyl aminomethylenephosphonic acid, m.p. 168°–171°C. (dec.)
8. Monoaniline salt of N-trichloroacetyl aminomethylenephosphonic acid, m.p. ~ 171°C. (dec.)
9. Monoaniline salt of N-dichloroacetyl aminomethylenephosphonic acid, m.p. 192°–193°C. (dec.)
10. Monoaniline salt of N-chloroacetyl aminomethylenephosphonic acid, m.p. 157°C.
11. Mono m-carboxyaniline salt of N-trichloroacetyl aminomethylenephosphonic acid, m.p. 200°–203°C.
12. Mono m-trifluoromethylaniline salt of N-trichloroacetyl aminomethylenephosphonic acid, m.p. 163°–164°C.
13. N-acetyl aminometylenephosphonic acid, m.p. 181°–186°C.
14. Diethyl N-acetyl aminomethylenephosphonate, b.p. 144°C. at 0.1 mm.

In determining the appropriate rates and times of application to sugar cane plants, it is necessary to consider both the chronological age of the plant and its stage of maturity since cane, depending upon the practice in different geographical areas, is grown from 9 to about 30 months before harvest. Application at a rate of from about 0.11 to 5.6 kg. per hectare can be made from about 2 to 8 weeks prior to the projected harvest date. Preferably, such applications are made from 3 to 7 weeks before said date.

The active ingredients of this invention can be conveniently applied to the plants as an aqueous solution or suspension. The active ingredient can, of course, be in its free acid form although it may be employed in the form of any of the above defined salts in order to improve such ancillary features of solubility or stability. For example, a liquid composition may be applied from a boom-spray, or a solid dust composition where the active component is diluted with an inert solid such as clay can be flown on the plants from an aircraft. Suitable liquid compositions include surfactants such as those enumerated in U.S. Pat. Nos. 3,224,865 and 3,245,775. Preferred surface active agents which are convenient to use in liquid compositions of this invention are of the non-ionic type such as alkyl phenoxy poly (ethyleneoxy) ethanols, polyethylene oxide adducts of fatty and resin acids, and long chain alkyl mercaptan adducts with ethylene oxide.

A particularly preferred carrier for the acids, esters or salts of this invention is water with about 0.1 to 2.0% by weight of surfactant added thereto. Alternatively, the aqueous carrier can be replaced by a non-toxic mineral oil as such, or as an oil-in-water or water-in-oil emulsion. It has been found convenient to apply the compositions to the plants in the form of aqueous solutions, suspensions or emulsions, the dilution being such that a spray volume of from about 10 to 30 liters of liquid per hectare will contain the desired dosage of active ingredient. It will be recognized, however, that higher or lower total spray volumes can be beneficially employed depending upon the particular dispensing apparatus and other factors well understood by those skilled in the art.

The specific examples which follow are presented as illustrative, non-limiting demonstrations of the useful and unexpected properties of the acids, esters and salts of this invention.

EXAMPLE I 0.5 Gram of Compound No. 1 is dissolved in 4 ml. water that contains as a surfactant about 0.25% (w./w.) nonylphenol which was ethoxylated to contain about 10.5 mols. of ethylene oxide per mol. of nonylphenol ("Tergitol NPX"). 0.6 ml. of this solution is deposited or dropped by means of a syringe with a fine needle on the spindle area at the top of the last visible dewlap of each of 20 stalks of sugar cane. (A dewlap is the junction between the blade of the leaf and the sheath which clasps the stalk). Ten of these stalks were harvested 4 weeks after such treatment and 10 more were harvested 5 weeks after such treatment.

The top 15 joints of the treated cane as well as those of similar untreated cane are removed, combined and analyzed in terms of juice purity and pol percent cane, following the so-called "press method" developed by T. Tanimoto, Hawaiian Planters Record, 57, 133 (1964). "Pol percent cane" is a polarmetric determination and equals the percentage of sucrose if the latter is the only substance in the solution which will rotate the plane of polarized light. In any event, determination of the pol percent cane is a standard and effective method for determining the sucrose content of sugar cane. The results are given below:

|  | FOUR WEEKS | | FIVE WEEKS | |
|---|---|---|---|---|
|  | Juice Purity | Pol% Cane | Juice Purity | Pol% Cane |
| Control (untreated) | 80.59 | 10.76 | 81.95 | 11.16 |
| Treated | 82.29 | 11.61 | 87.76 | 15.45 |

These results clearly show an improvement in both sucrose yield and juice purity of the treated plants.

EXAMPLE II

The procedures described in the preceding example are repeated with the same compound on another variety of sugar cane plants about 5 months later with the following results:

|  | FOUR WEEKS | | FIVE WEEKS | |
|---|---|---|---|---|
|  | Juice Purity | Pol% Cane | Juice Purity | Pol% Cane |
| Control (untreated) | 61.15 | 5.64 | 64.10 | 6.87 |
| Treated | 85.91 | 12.53 | 83.76 | 12.20 |

The treated plants again clearly demonstrate a substantial gain in both of the factors measured.

EXAMPLE III

The procedures described in the preceding examples are repeated about 10 months after the second testing using various other compounds of this invention with the following results:

|  | FOUR WEEKS | | FIVE WEEKS | |
|---|---|---|---|---|
|  | Juice Purity | Pol% Cane | Juice Purity | Pol% Cane |
| Control (untreated) | 71.80 | 7.56 | 71.11 | 7.45 |
| Treated: | | | | |
| No. 5 | 83.50 | 11.14 | 82.42 | 10.35 |
| No. 7 | 85.62 | 12.40 | 83.77 | 10.61 |
| No. 10 | 71.44 | 7.93 | 78.05 | 9.21 |
| No. 11 | 79.60 | 9.98 | 66.27 | 6.19 |
| No. 12 | 77.11 | 9.52 | 79.13 | 9.84 |

Desirable improvements of each measured factor at both harvests are observed with Compounds Nos. 5, 7 and 12. Compound No. 10 is equal to the control at 4 weeks, while Compound No. 11 is below the control at 5 weeks. However, each of these latter compounds demonstrates a substantial increase in both factors at the other date of harvest.

EXAMPLE IV

The procedures described in the preceding examples are repeated about 14 months after the third testing with Compound No. 9. The following results were obtained:

|  | FOUR WEEKS | | FIVE WEEKS | |
|---|---|---|---|---|
|  | Juice Purity | Pol% Cane | Juice Purity | Pol% Cane |
| Control (untreated) | 53.61 | 4.43 | 61.40 | 5.45 |
| Treated | 57.29 | 5.23 | 62.47 | 6.02 |

The treated plants at both harvests demonstrated an increase in each of the factors measured.

EXAMPLE V

The procedures described in the preceding examples are repeated about 1 month after the third testing with Compound No. 13. The following results were obtained:

|  | FOUR WEEKS | | FIVE WEEKS | |
| --- | --- | --- | --- | --- |
|  | Juice Purity | Pol% Cane | Juice Purity | Pol% Cane |
| Control (untreated) | 64.24 | 6.57 | 67.32 | 7.19 |
| Treated | 62.56 | 6.43 | 76.73 | 9.53 |

Although the treated plants showed decreased measurements at the earlier harvest, both of the factors measured showed substantial increases at the later harvest.

Although the invention has been described herein with respect to specific embodiments, the details thereof are not to be construed as limitations except to the extent defined in the following claims.

What is claimed is:

1. A method for increasing the sucrose content of sugar cane plants which comprises applying to said plants, from about 2 to 8 weeks prior to harvest, an effective amount of a compound selected from those of the formula

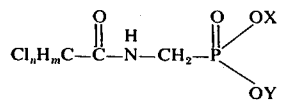

wherein X and Y represent hydrogen or lower alkyl, $n$ is an integer from zero to three, $m$ is an integer from zero to three, and the sum of $m + n$ is three; and certain salts thereof, which salts are selected from the group consisting of alkali metal, ammonium, lower alkyl and lower alkanol amine, aniline and substituted aniline.

2. A method as defined in claim 1 wherein application is at a rate of about 0.11 to 5.6 kg. per hectare.

3. A method as defined in claim 1 wherein application is made from about 3 to 7 weeks prior to harvest.

4. A method as defined in claim 2 wherein application is made from about 3 to 7 weeks prior to harvest.

5. A method as defined in claim 1 wherein said compound is a salt.

6. A method as defined in claim 5 wherein said salt is a lower alkyl amine salt.

7. A method as defined in claim 5 wherein said salt is a lower alkanol amine salt.

8. A method as defined in claim 5 wherein said salt is an aniline salt.

9. A method as defined in claim 1 wherein $n$ is three and $m$ is zero.

10. A method as defined in claim 1 wherein $n$ is two and $m$ is one.

11. A method as defined in claim 1 wherein $n$ is one and $m$ is two.

12. A method as defined in claim 1 wherein $n$ is zero and $m$ is three.

13. A method as defined in claim 1 wherein the compound is N-trichloroacetyl aminomethylenephosphonic acid.

14. A method as defined in claim 1 wherein the compound is monopotassium salt of N-trichloroacetyl aminomethylenephosphonic acid.

15. A method as defined in claim 1 wherein the compound is monoethanolamine salt of N-trichloroacetyl aminomethylenephosphonic acid.

16. A method as defined in claim 1 wherein the compound is monoaniline salt of N-chloroacetyl aminomethylenephosphonic acid.

17. A method as defined in claim 1 wherein the compound is mono m-carboxyaniline salt of N-trichloroacetyl aminomethylenephosphonic acid.

18. A method as defined in claim 1 wherein the compound is mono m-trifluoromethylaniline salt of N-trichloroacetyl aminomethylenephosphonic acid.

19. A method as defined in claim 1 wherein the compound is N-acetyl aminomethylenephosphonic acid.

* * * * *